United States Patent
Le Couedic et al.

(10) Patent No.: US 6,309,390 B1
(45) Date of Patent: Oct. 30, 2001

(54) DEVICE FOR BACKBONE OSTEOSYNTHESIS WITH OFFSET INTERVERTEBRAL FIXING ROD

(75) Inventors: Régis Le Couedic, Saint-Médard-en-Jalles; Christian Baccelli, Saint-Médard-d'Eyrans; Frédéric Conchy, Bordeaux, all of (FR)

(73) Assignee: Stryker France S.A. (FR)

( * ) Notice: Subject to any disclaimer, the term of this patent is extended or adjusted under 35 U.S.C. 154(b) by 0 days.

(21) Appl. No.: 09/402,556
(22) PCT Filed: Apr. 3, 1998
(86) PCT No.: PCT/FR98/00679
 § 371 Date: Mar. 7, 2000
 § 102(e) Date: Mar. 7, 2000
(87) PCT Pub. No.: WO98/44859
 PCT Pub. Date: Oct. 15, 1998

(30) Foreign Application Priority Data

Apr. 4, 1997 (FR) .................................................. 97 04133

(51) Int. Cl.[7] .................................................... A61B 17/70
(52) U.S. Cl. ............................................................ 606/61
(58) Field of Search .......................................... 606/60, 61

(56) References Cited

U.S. PATENT DOCUMENTS

| 5,254,118 | * | 10/1993 | Mirkovic ................................. 606/61 |
| 5,437,669 | * | 8/1995 | Yuan et al. ............................. 606/61 |
| 5,474,551 | * | 12/1995 | Finn et al. .............................. 606/61 |
| 5,584,831 | * | 12/1996 | McKay .................................... 606/61 |
| 5,776,135 | * | 7/1998 | Errico et al. ........................... 606/61 |

* cited by examiner

Primary Examiner—Gene Mancene
Assistant Examiner—Eduardo C. Robert
(74) Attorney, Agent, or Firm—Blakely Sokoloff Taylor & Zafman

(57) ABSTRACT

A device for backbone osteosynthesis having a bone anchoring element, a linking rod for linking the anchoring element with other anchoring elements, an intermediate element, a swivel linkage between the intermediate element first part and the bone anchoring element, a clamping linkage between the intermediate element second part and the intervertebral linking rod, and a locking mechanism for the swivel and the clamping linkages. The clamping linkage includes a clip with two branches laterally adjusted from the swivel and open opposite same. The locking mechanism acts on the branches in the region of their free ends so as to stress the latter towards each other.

9 Claims, 5 Drawing Sheets

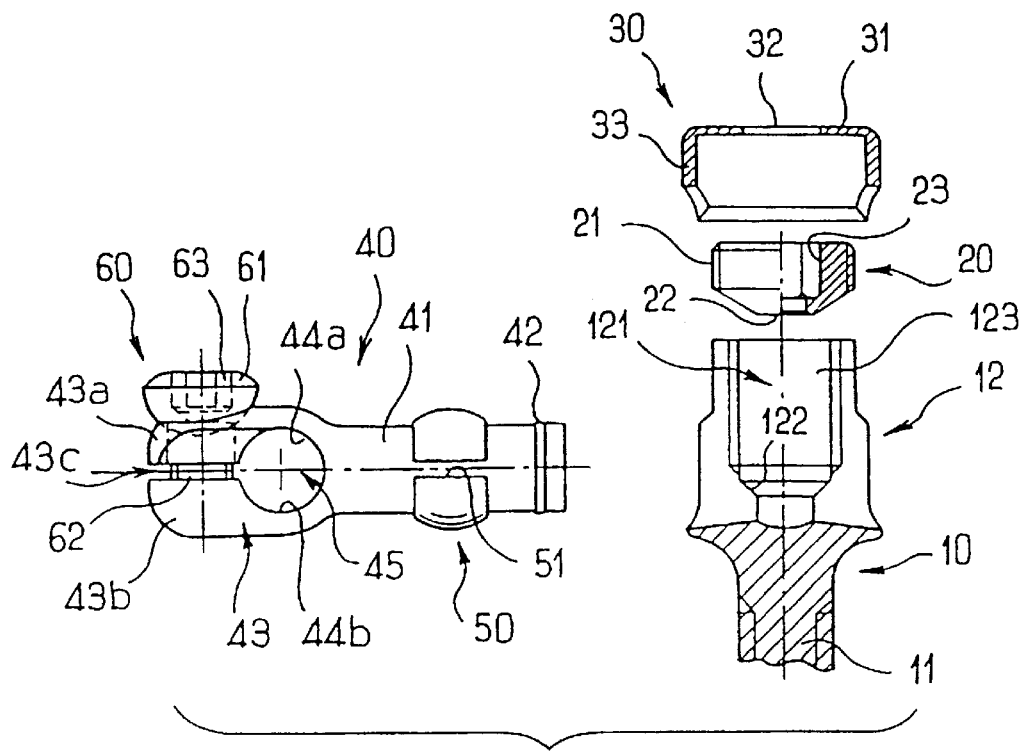
FIG_1
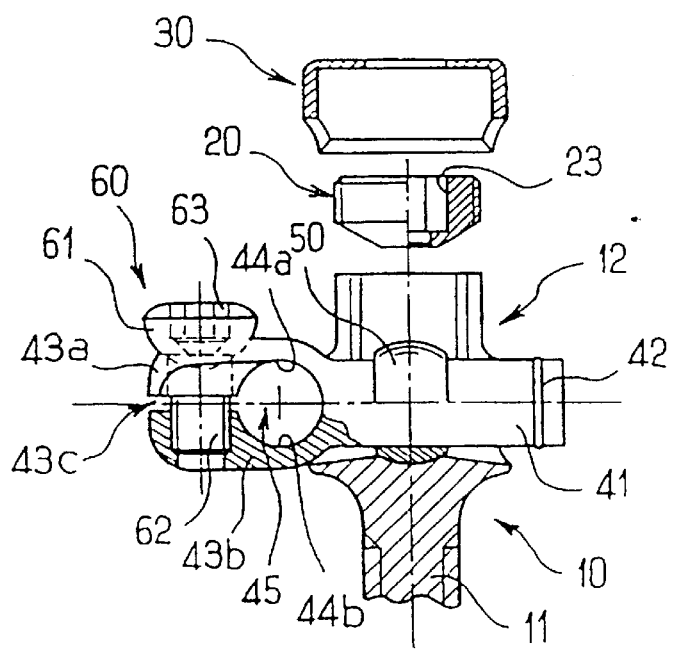
FIG_2

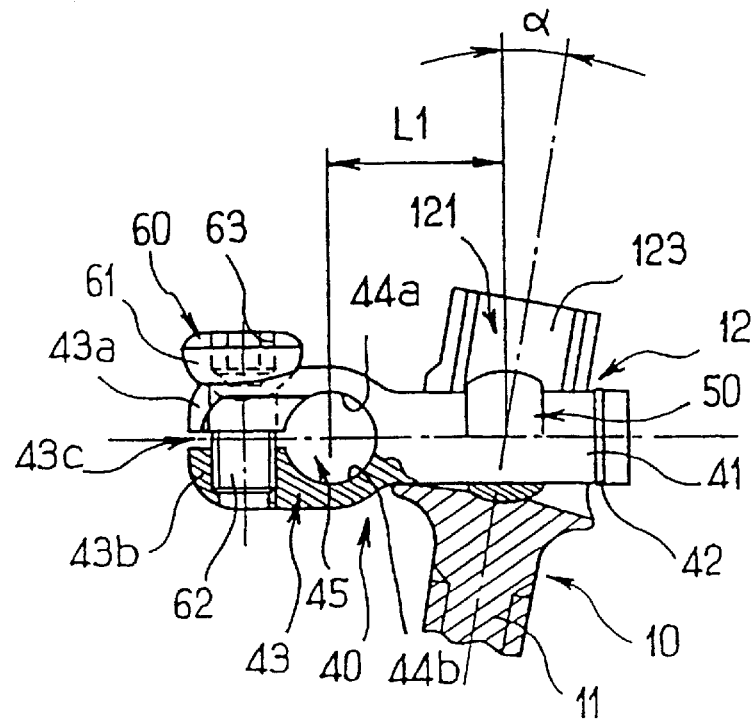
FIG_3
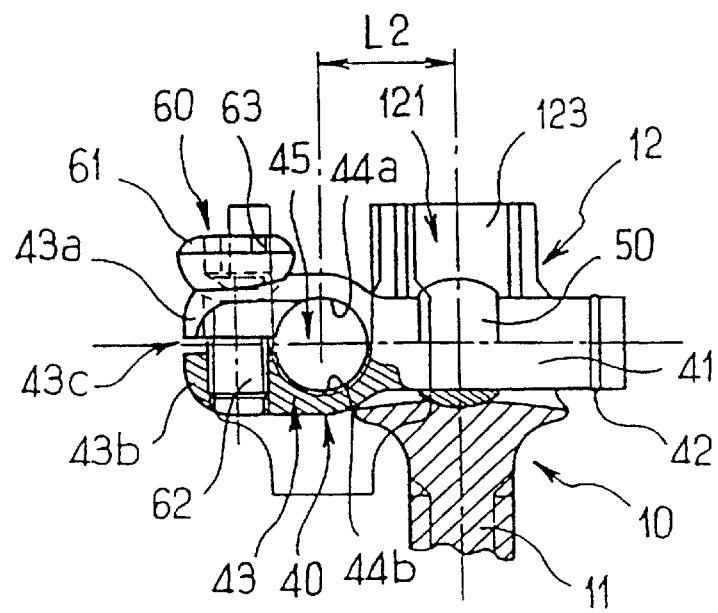
FIG_4

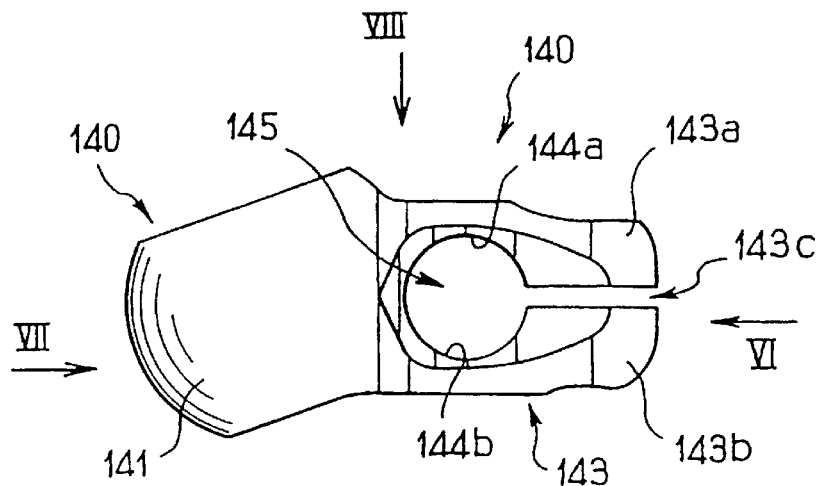
FIG_5
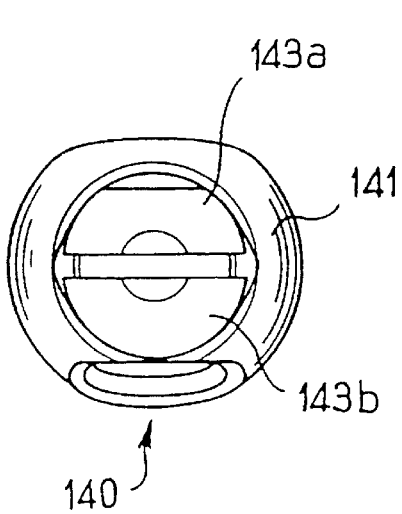
FIG_6
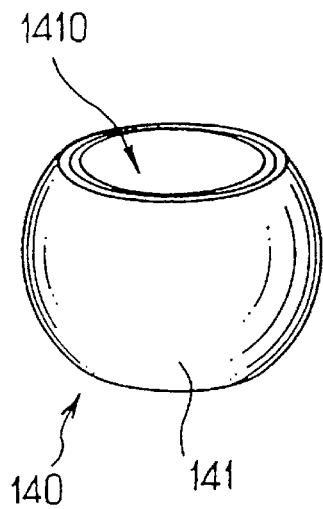
FIG_7
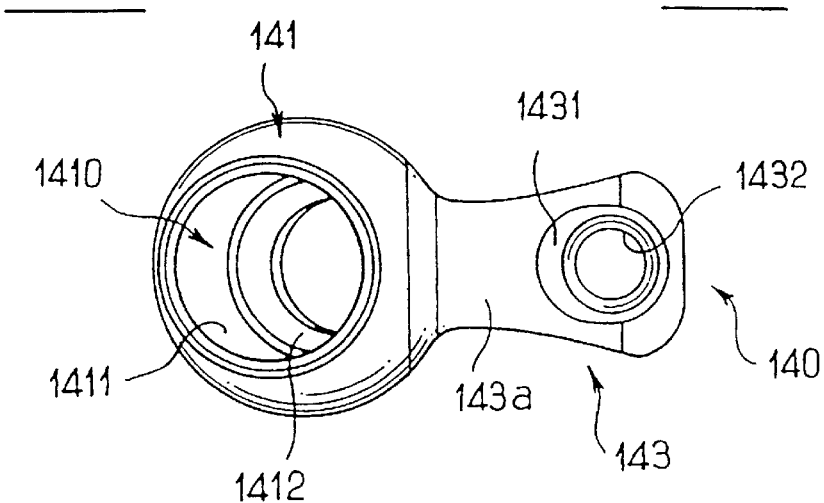
FIG_8

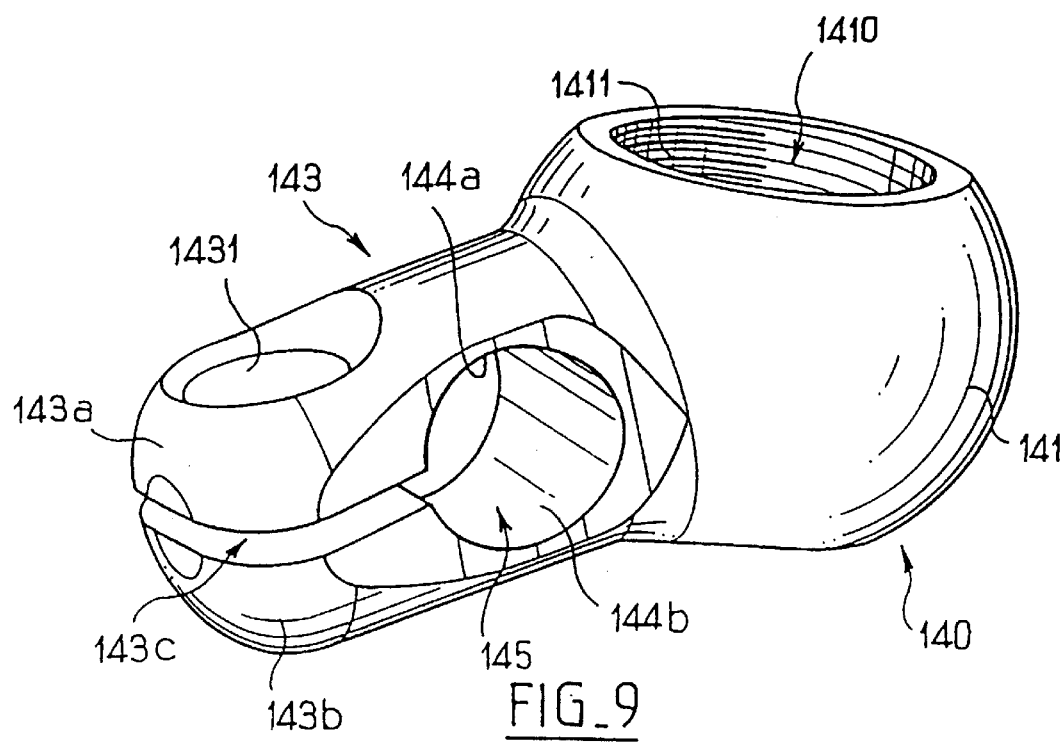
FIG_9
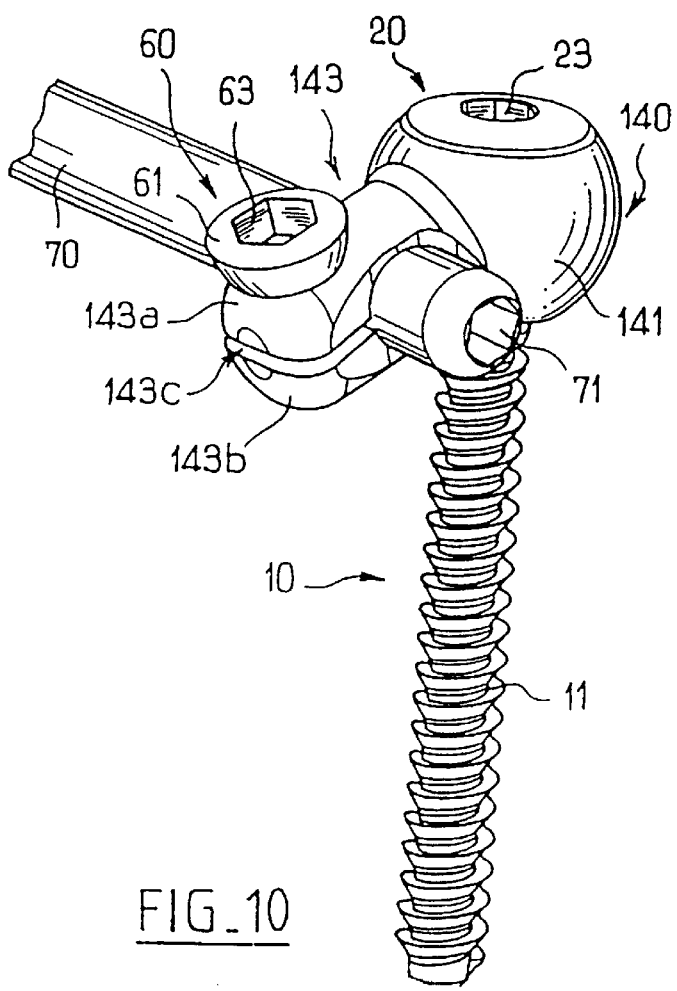
FIG_10

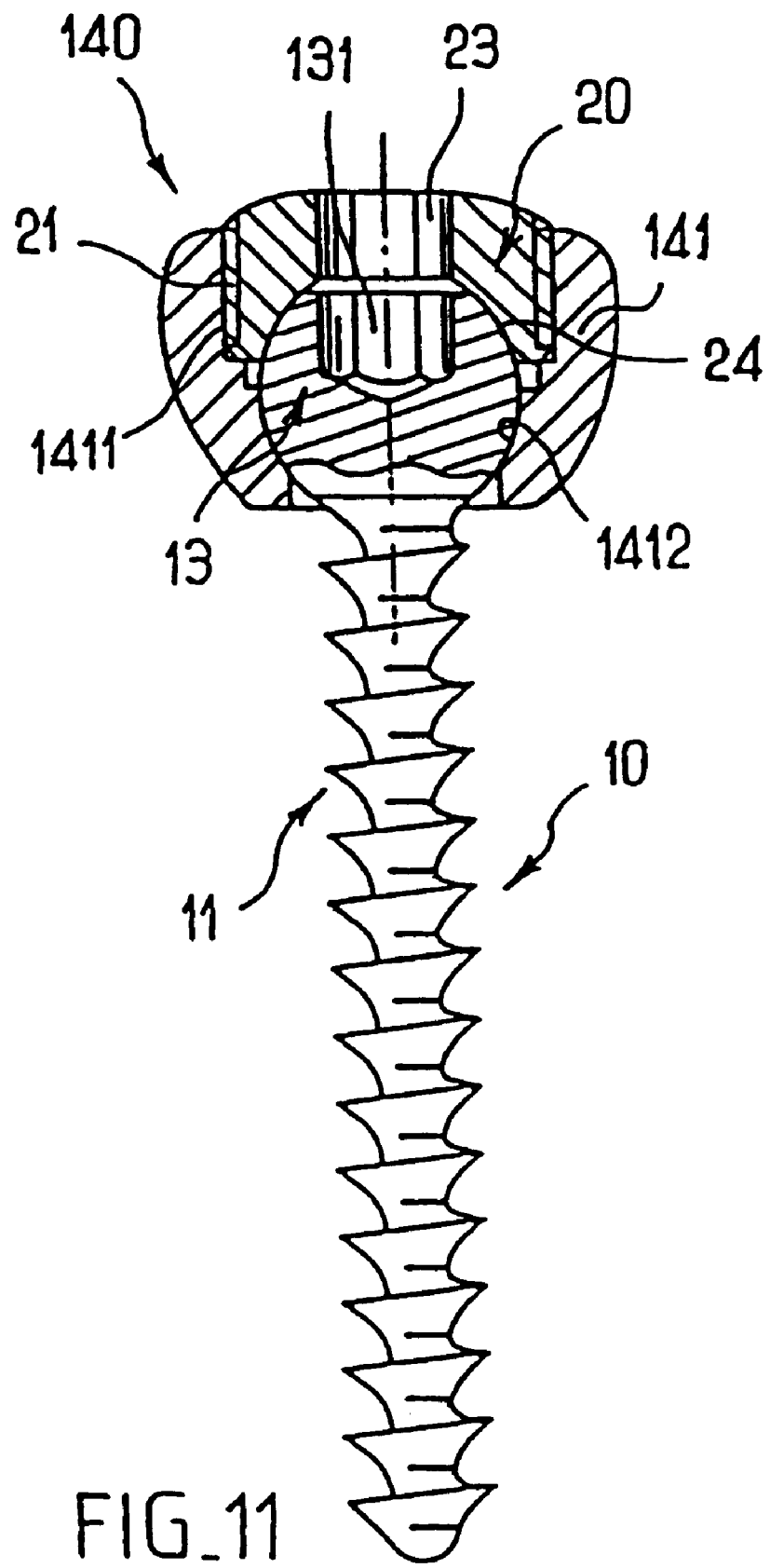
FIG_11

DEVICE FOR BACKBONE OSTEOSYNTHESIS WITH OFFSET INTERVERTEBRAL FIXING ROD

The present invention relates in general terms to devices for osteosynthesis of the spine.

BACKGROUND OF THE INVENTION

An implant for osteosynthesis of the spine is already known, in particular from document FR-A-2 659 546, which implant comprises a pedicular screw provided with a head that is generally tuningfork-shaped, capable of directly receiving a cylindrical rod for linking vertebrae together. A split ring and a threaded clamping plug acting between the two branches of the head enable the assembly to be locked with angular adjustment being possible between the rod and the axis of the pedicular screw.

Installing that type of implant does not present the surgeon with any major difficulty, providing the heads of the various pedicular screws are sufficiently well aligned with one another, since under those circumstances the intervertebral link rod can be put into place relatively easily in said heads, without excessive stresses or twisting.

However, particularly depending on the type of pedicular aiming performed by the surgeon, and also depending on the orientation of the pedicles specific to each patient, it often happens that the axes of the pedicular screws are significantly inclined relative to the sagittal plane, and as a result, the housings for receiving the intervertebral link rod and as defined by the heads of the various screws can be very significantly out of alignment.

Under such circumstances, the solution which consists in deforming the rod very significantly so as to force it to follow the imposed path is either impracticable because of the considerable deformation forces that would be required, or else dangerous because it runs the risk of weakening the rod.

Various other devices are known for the purpose of making it possible to fix and lock a rod that is laterally offset relative to a pedicular screw.

Examples of such devices are given in the following documents: DE-A-195 12 709, U.S. Pat. Nos. 5,575,791, 5,002,542, WO-A-95 02372, and WO-A-96 29947.

Nevertheless, all of those known devices suffer from drawbacks. Thus, some of them are of considerable size, particularly in height, which is quite undesirable and considerably reduces the advantage in terms of compactness of "tuningfork"-type screw devices of the kind described above. Others are complex in structure, having numerous parts. Others are structurally incapable of receiving rods at an appropriate distance from the pedicles, which distance is moreover imposed by the "tuningfork"-type screws. Finally, some of those known devices are unsuitable for locking the rod relative to its anchor point in the bone in a manner that is sufficiently firm and strong.

BRIEF SUMMARY OF THE INVENTION

An object of the present invention is thus to mitigate those drawbacks and to propose means that are simple, and therefore do not significantly complicate installation operations, making it possible to connect a bone implant of conventional type rigidly to an intervertebral link rod while the rod is significantly off-axis relative to the bone implant.

Another object of the invention is to be able to use the same type of pedicular screw in all of the vertebrae regardless of the sizes of such offsets.

Yet another object is also to propose off-axis fixing for a link rod on a particular type of sacral fixing.

Thus, the present invention provides an osteosynthesis device for the spine, the device comprising a bone anchor element, an intervertebral link rod suitable for connecting said bone anchor element to other anchor elements, an intermediate element, a ball-and-socket link between a first portion of the intermediate element and the bone anchor element, a clamping link between a second portion of the intermediate element and the intervertebral link rod, and locking means for locking the ball-and-socket link and the clamping link, which device is characterized in that said clamping link is constituted by a clamp having two branches extending laterally from the ball-and-socket link and open away therefrom, and in that the means for locking the clamping link include a clamping member acting on said branches in the region of their free ends in such a manner as to urge said ends towards each other.

Preferred, but non-limiting, features of the device of the invention are as follows:

the ball-and-socket link comprises a generally spherical seat provided in a head of the bone anchor element and an essentially complementary compressible ring received in said seat, and said first portion of the intermediate element comprises a cylindrical appendix received in said ring;

said cylindrical appendix is of circular section;

said cylindrical appendix is of a length such that prior to locking, it is capable of sliding relative to the ring to vary the axial offset between the bone anchor element and the intervertebral link rod;

said cylindrical appendix, in the region of its free end, presents an enlargement for preventing said appendix from escaping freely from the ring prior to locking;

the ring is a split ring, and the enlargement has a diameter such that the appendix can be engaged by force through the ring with temporary elastic deformation thereof;

said first portion of the intermediate element has a housing for a head of a bone anchor element, and the ball-and-socket link has a generally spherical seat defined in said housing and an essential complementary spherical wall formed on said head;

the means for locking the ball-and-socket link comprise a threaded plug screwed into an opening of said housing remote from its seat; and said branches of the clamp define an empty passage between them suitable for receiving the intervertebral link rod, and said clamping member is constituted by a screw.

BRIEF DESCRIPTION OF THE DRAWINGS

Other features, objects, and advantages of the present invention will appear better on reading the following detailed description of a preferred embodiment thereof, given by way of example and made with reference to the accompanying drawings, in which:

FIG. 1 is an exploded cross-section view through an osteosynthesis device constituting a first embodiment of the invention;

FIG. 2 is a cross-section view after the FIG. 1 device has been partially assembled;

FIGS. 3 and 4 are cross-section views of the device of FIGS. 1 and 2 in two different locking positions, some of the members of the device being omitted for simplification purposes;

FIG. 5 is a profile view of a part of an osteosynthesis device constituting a second embodiment of the invention;

FIG. 6 is a front end view seen along arrow VI of FIG. 5;

FIG. 7 is a back end view seen along arrow VII of FIG. 5;

FIG. 8 is a plan view seen along arrow VIII of FIG. 5;

FIG. 9 is a perspective view of the element shown in FIGS. 5 to 8;

FIG. 10 is a perspective view of the osteosynthesis device constituting the second embodiment of the invention when in the assembled state; and FIG. 11 is a cross-section view of the device of FIG. 10.

DETAIL DESCRIPTION OF THE INVENTION

With reference to the drawings, initially to FIGS. 1 to 4, there is shown a first embodiment of an osteosynthesis device for the spine, which device comprises a bone anchor element 10, in this case in the form of a pedicular screw, having a head 12 and a threaded portion 11 for co-operating with the bone.

The head 12 has two branches 123 generally in the form of a tuning fork, having an inside thread and defining a cavity 121 with a spherical seat 122 formed at the bottom thereof.

A threaded plug 20 having an outside thread 21 and a generally plane or concave bearing surface 22 is suitable for being screwed between the two branches by means of a tool inserted into a tightening socket 23, as explained below.

Finally, a cap 30 possessing a downwardly-extending peripheral skirt 33 and a top face 31 having an opening 32 formed therein for the above-mentioned tightening tool can be applied to the top of the head 12, covering the branches 123, in particular so as to prevent said branches from splaying apart during the above-mentioned tightening.

The device in this first embodiment also has an element 40 having a first end, to the right in FIG. 1, defining a circularly cylindrical rod 41. This rod 41 has a ring 50 placed thereon, with the ring having an outer surface that is generally spherical and a cylindrical through passage of diameter slightly greater than the diameter of the rod 41. The ring is split at 51 to impart a certain degree of elastic deformability thereto, as explained below.

In the vicinity of its free end, the rod 41 has a slightly-projecting rib 42 which serves to prevent the ring 51 from escaping freely from the rod 41 once it has been put into place thereon by being forced over said rib.

At its opposite end, the element 40 has a clamp-forming portion 43 possessing two branches 43a and 43b that are disposed one above the other. Near the roots of the two branches, each of them possesses a respective essentially semicylindrical recess 44a, 44b, with the two recesses together defining a cylindrical passage 45 oriented perpendicularly to the axis of the rod 41.

Between said recesses and their free ends, the branches 43a and 43b are separated by a gap 43c and they have respective cylindrical passages extending in alignment perpendicularly to the passage 45 and to the rod 41. The upper passage is smooth while the lower passage is tapped.

A clamping screw 60 is provided to be inserted and tightened in said passages, this screw comprising in conventional manner a threaded rod 62, a larger head 61, and a socket 63 formed in the head 61 to receive a tightening tool.

It may be observed at this point that the assembly constituted by the pedicular screw 10, the threaded plug 20, the cap 30, and the ring 50, is as described in document FR-A-2 659 546.

FIG. 2 shows the FIG. 1 device in a partially assembled state.

Thus, once the pedicular screw 10 has been anchored in a vertebra, the rod 41 fitted with the ring 50 has been placed in the space 121 inside the head 12 of the screw 10, with the ring 50 having its bottom region pressing against the concave spherical bearing surface 122 formed at the bottom of said inside space.

Once the element 40 is in the appropriate position, the plug 20 is premounted in the head 12, the cap is put into place on top of the plug, and the plug 20 is tightened using a tool.

The plug 20 then compresses and deforms the ring 50 so as to lock the rod 40 in the position desired both angularly and in translation along its axis.

The passage 45 is designed to receive an intervertebral link rod (not shown) which is connected to other bone anchor elements that can be identical or otherwise.

By clamping together the branches 43a and 43b, tightening the screw 60 serves to lock the above-mentioned link rod in place.

Thus, the above-described device makes it possible with means that are simple to manufacture and handle to fix an intervertebral link rod in off-axis and optionally vertically-offset manner as compared with a conventional type of implant as described in particular in FR-A-2 659 546, and it do so with a very wide range of adjustment possibilities obtained firstly by selecting the position of the ring 50 on the rod 41 prior to locking by means of the plug 20 and secondly by selecting the angular orientation of said rod 41, likewise prior to locking by means of the plug 20.

Thus, FIG. 3 of the drawings shows the case where the axial offset between the pedicular screw 10 and the link rod has a certain value L1, while the angle [α] between the axis of the pedicular screw 10 and the plane perpendicular to the axis of the rod 41 is not zero.

In the case of FIG. 4, the above-mentioned axial offset has been reduced to a value L2 that is less than L1, while the axis of the pedicular screw 10 is situated in the plane perpendicular to the axis of the rod 41 ([α]=0[°]).

Where necessary, the position of the element 40 relative to the intervertebral link rod can be adjusted prior to locking by means of the screw 60.

With reference now to FIGS. 6 to 11, a second embodiment of an osteosynthesis device of the invention for the spinal column is shown. In these figures, elements or portions identical or similar to those of the preceding embodiment are, whenever possible, designated by the same reference symbols.

This device comprises a screw 10, more particularly for anchoring in the sacrum, said screw comprising a threaded rod 11 surmounted by a spherical head 13 in which a hollow socket 131 for tightening purposes is formed at its end remote from the threaded rod.

The device comprises an element 140 having a portion 141 in the form of a hollow and generally spherical body 141. The cavity 1410 defined in said body has a tapped cylindrical portion 1411 and beneath the tapping, a concave spherical seat 1412 having the same diameter as that of the spherical head 13 of the sacral fixing screw 10.

This cavity 1410 opens upwards via the tapping and downwards via an orifice situated in the bottom of the spherical seat and of a size that is perceptibly greater than the section of the threaded rod 11 of the screw 10.

A plug 20 possessing an outside thread 21 suitable for co-operating with the tapping 1411 can be engaged inside the cavity 1410 from above by being screwed in, and the top face of the plug has a through socket 23 enabling it to be tightened by means of a tool. Around the outlet of the socket 23, the bottom face of the plug 20 defines a hollow spherical surface 24 having the same diameter as the spherical head 13 of the screw 10.

Projecting laterally from the body 141, the element 140 also has a clamp-forming extension 143 analogous to the clamp 43 of FIGS. 1 to 4.

More precisely, two branches 143*a* and 143*b* extend parallel to each other, and near their roots they define two respective essentially semicylindrical setbacks 144*a* and 144*b* defining a through passage 145 for an intervertebral link rod 70, shown in part in FIG. 10.

Between this passage and their free ends, the branches 143*a* and 143*b* are separated by a gap 143*c*, with one of them having a smooth bore 1431 passing therethrough and the other having a tapped bore 1432 for receiving a clamping screw 60 identical to that of FIGS. 1 to 4.

The device is assembled as follows:

by inserting the sacral fixing screw 10 in the cavity 1410 of the body 141 of the part 140 so that its head 13 ends its stroke in said cavity, the threaded portion 11 then projecting beneath the body 141 ready for screwing into the sacrum by means of a tool engaged in the socket 131;

by screwing the plug 20 into the cavity 141 over the head 13 but without tightening it, and then giving the clamp 143 which receives the link rod 70 the desired inclination relative to the axis of the screw 10, after which the plug is tightened by means of a tool engaged in the socket 23; the head 13 of the screw is then firmly locked relative to the element 140 in the desired position; and by locking the link rod 70 in the passage 145 by means of the screw 60 (which operation can be also be performed prior to at least one of the preceding steps).

Thus, this embodiment makes it possible with a single part 140 to provide an off-center link between a sacral fixing screw and an intervertebral link rod which is connected to vertebrae adjacent to the sacrum by other means which are conventional per se.

It may be observed at this point that the generally rounded shape of the surfaces of the part 140 (and also of the clamp-forming portion 43 in the preceding embodiment) serve to minimize lesions in adjacent tissue.

Naturally, the various components of the two above-described osteosynthesis devices are made out of a biocompatible material such as stainless steel or a titanium alloy.

The present invention is not limited in any way to the embodiments described and shown, and the person skilled in the art can apply any variation or modification thereto within the spirit to the invention.

What is claimed is:

1. An osteosynthesis device for a spine, the device comprising:

a bone anchor element, an intervertebral link rod suitable for connecting said bone anchor element to other anchor elements, an intermediate element, a ball-and-socket link between a first portion of the intermediate element and the bone anchor element, a clamping link between a second portion of the intermediate element and the intervertebral link rod, and locking means for locking the ball-and-socket link and the clamping link, wherein said clamping link includes a clamp having two branches extending laterally from the ball-and-socket link, open away therefrom, and holding the intervertebral link rod captive therebetween, and the locking means acts on the clamp in an end region of said branches situated, relative to the rod, on an opposite side to the ball-and-socket link, so as to urge said branches towards each other.

2. A device according to claim 1, wherein the ball-and-socket link comprises a generally spherical seat provided in a head of the bone anchor element and an essentially complementary compressible ring received in said seat, and said first portion of the intermediate element comprises a cylindrical appendix received in said ring.

3. A device according to claim 2, wherein said cylindrical appendix is of circular section.

4. A device according to claim 2 or 3, wherein said cylindrical appendix is of a length such that prior to locking, it is capable of sliding relative to the ring to vary an axial offset between the bone anchor element and the intervertebral link rod.

5. A device according to claim 4, wherein said cylindrical appendix, in a region of its free end, presents an enlargement for preventing said appendix from escaping freely from the ring prior to locking.

6. A device according to claim 5, wherein the ring is a split ring and the enlargement has a diameter such that the appendix can be engaged by force through the ring with temporary elastic deformation thereof.

7. A device according to claim 1, wherein said first portion of the intermediate element has a housing for a head of a bone anchor element, and the ball-and-socket link has a generally spherical seat defined in said housing and an essentially complementary spherical wall formed on said head.

8. A device according to claim 7, wherein the means for locking the ball-and-socket link comprise a threaded plug screwed into an opening of said housing remote from its seat.

9. A device according to claim 1 wherein said branches of the clamp define an empty passage between them suitable for receiving the intervertebral link rod, and said clamping member includes a screw.

\* \* \* \* \*

UNITED STATES PATENT AND TRADEMARK OFFICE
CERTIFICATE OF CORRECTION

PATENT NO. : 6,309,390 B1  Page 1 of 1
DATED : October 30, 2001
INVENTOR(S) : Le Couedic et al.

It is certified that error appears in the above-identified patent and that said Letters Patent is hereby corrected as shown below:

<u>Title page,</u>
Item [54], please delete title "DEVICE FOR BACKBONE OSTEOSYNTHESIS WITH OFFSET INTERVERTEBRAL FIXING ROD" and insert -- AN OSTEOSYNTHESIS DEVICE FOR THE SPINE WITH AN OFF-AXIS FIXING FOR AN INTERVERTEBRAL ROD --.

Item [56], References Cited, please insert the following U.S. PATENT and FOREIGN PATENT DOCUMENTS:

U.S. PATENT DOCUMENTS

-- 5,575,791    11/19/96    Lin
   5,002,542    3/26/91     Frigg --

--    FOREIGN PATENT DOCUMENTS

WO 95 02372   1/26/95    PCT
      DE 19512709   10/10/96   Deutschland
      WO 96 29947   10/3/96    PCT --

Signed and Sealed this

Sixth Day of May, 2003

JAMES E. ROGAN
*Director of the United States Patent and Trademark Office*